(12) United States Patent
Onishi et al.

(10) Patent No.: US 6,869,423 B2
(45) Date of Patent: Mar. 22, 2005

(54) DISPOSABLE DIAPER

(75) Inventors: Kazuaki Onishi, Kagawa-ken (JP); Yasushi Sayama, Kagawa-ken (JP); Hiroyuki Tanji, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 351 days.

(21) Appl. No.: 10/073,882

(22) Filed: Feb. 14, 2002

(65) Prior Publication Data

US 2002/0111594 A1 Aug. 15, 2002

(30) Foreign Application Priority Data

Feb. 15, 2001 (JP) ........................................ 2001-038551

(51) Int. Cl.⁷ .............................................. A61F 13/15
(52) U.S. Cl. .............. 604/385.01; 604/378; 604/385.28
(58) Field of Search ................................ 604/378, 379, 604/385.17, 385.01, 385.28, 385.29, 383

(56) References Cited

U.S. PATENT DOCUMENTS 2,837,095 A * 6/1958 Stevenson ................... 604/354
4,988,345 A * 1/1991 Reising ....................... 604/368
5,176,672 A * 1/1993 Bruemmer et al. ..... 604/385.19
5,986,167 A * 11/1999 Arteman et al. ............ 604/380
6,699,228 B1 * 3/2004 Chmielewski et al. . 604/385.28

OTHER PUBLICATIONS

Japanese Patent Application No. 1996–196565A abstract figures only.

* cited by examiner

Primary Examiner—Jacqueline Stephens
(74) Attorney, Agent, or Firm—Lowe Hauptman Gilman & Berner, LLP (57) ABSTRACT

A disposable diaper includes a basic absorbent batt structure and a supplementary absorbent batt structure placed on the basic absorbent batt structure. The diaper is formed with a feces receiving space surrounded by the supplementary absorbent batt structure and bottom and side surfaces of a cavity and extending from a crotch region toward a front waist region so that an upper opening of the cavity is partially uncovered in the crotch region 31 and thereby forms a feces inlet leading to the space.

12 Claims, 10 Drawing Sheets

DISPOSABLE DIAPER

BACKGROUND OF THE INVENTION

This invention relates to a disposable diaper for absorption and containment of body wastes and the like.

Japanese Patent Application No. 1996-196565A discloses a disposable diaper comprising a liquid-pervious topsheet, a liquid-impervious backsheet and a liquid-absorbent core interposed between these sheets wherein the core consists of an upper layer core and a lower layer core. The upper layer core consists of, in turn, a front core extending from a front waist region toward a crotch region and a rear core extending from a rear waist region toward the crotch region. In this diaper, a rear end of the front core and a front end of the rear core are spaced from each other in a longitudinal direction of the diaper by a given dimension, and the topsheet covering the upper surface of the upper core is folded back along the rear end of the front core and the front end of the rear core toward the lower layer core and tucked between the upper core and lower layer core.

In this diaper of well known art, a pocket is formed between the front core and the lower layer core so as to secured an opening from the front waist region toward the crotch region and another pocket is formed between the rear core and the lower layer core so as to open from the rear waist region toward the crotch region.

However, the diaper disclosed in the Application has no arrangement to space the front and rear ends of the rear core and the front core, respectively from the lower layer core, so it is difficult to provide a space for receiving feces between the front and rear cores, on one hand, and the lower layer core, on the other hand. With this diaper of well known art, if the pocket opening is secured, only a small space is formed between the front and rear cores and the lower layer core. However, a wearer's body weight exerted on the diaper from the side of the topsheet downward in a direction of the diaper thickness will collapse the space and closes the pocket opening. Upon closure, it is no more possible for these pockets to receive feces and, in consequence, feces may flow over the front and rear cores and cling to the wearer's skin.

SUMMARY OF THE INVENTION

It is an object of this invention to offer a disposable diaper provided with a feces receiving space which is not easily collapsed and able to prevent any quantity of feces from clinging to a wearer's skin.

According to this invention, there is a disposable diaper having a front waist region, a rear waist region and a crotch region, comprising a basic absorbent batt structure having a liquid-pervious body facing surface and a liquid-impervious garment facing surface and at least one supplementary absorbent batt structure having a liquid-pervious body facing surface and an opposite inner surface. The supplementary absorbent batt structure is placed upon the body facing surface of the basic absorbent batt structure so as to extend from the front waist region toward the crotch region.

The basic absorbent batt structure is formed in a transversely middle region of the body facing surface thereof with a cavity so as to extend from the crotch region toward the front waist region. The supplementary absorbent batt structure covers an upper opening of the cavity extending in the front waist region and partially covers the upper opening of the cavity extending in the crotch region, and a feces receiving space is formed between the supplementary absorbent batt structure and the cavity so as to extend from the crotch region toward the front waist region and the upper opening of the cavity is partially uncovered in the crotch region to define an inlet being contiguous to the feces receiving space.

DETAILED DESCRIPTION OF THE PREFERRED EMBODIMENTS

Details of a disposable diaper according to this invention will be more fully understood from the description on an open-type diaper given hereunder as an example with reference to the accompanying drawings.

Figure 1:
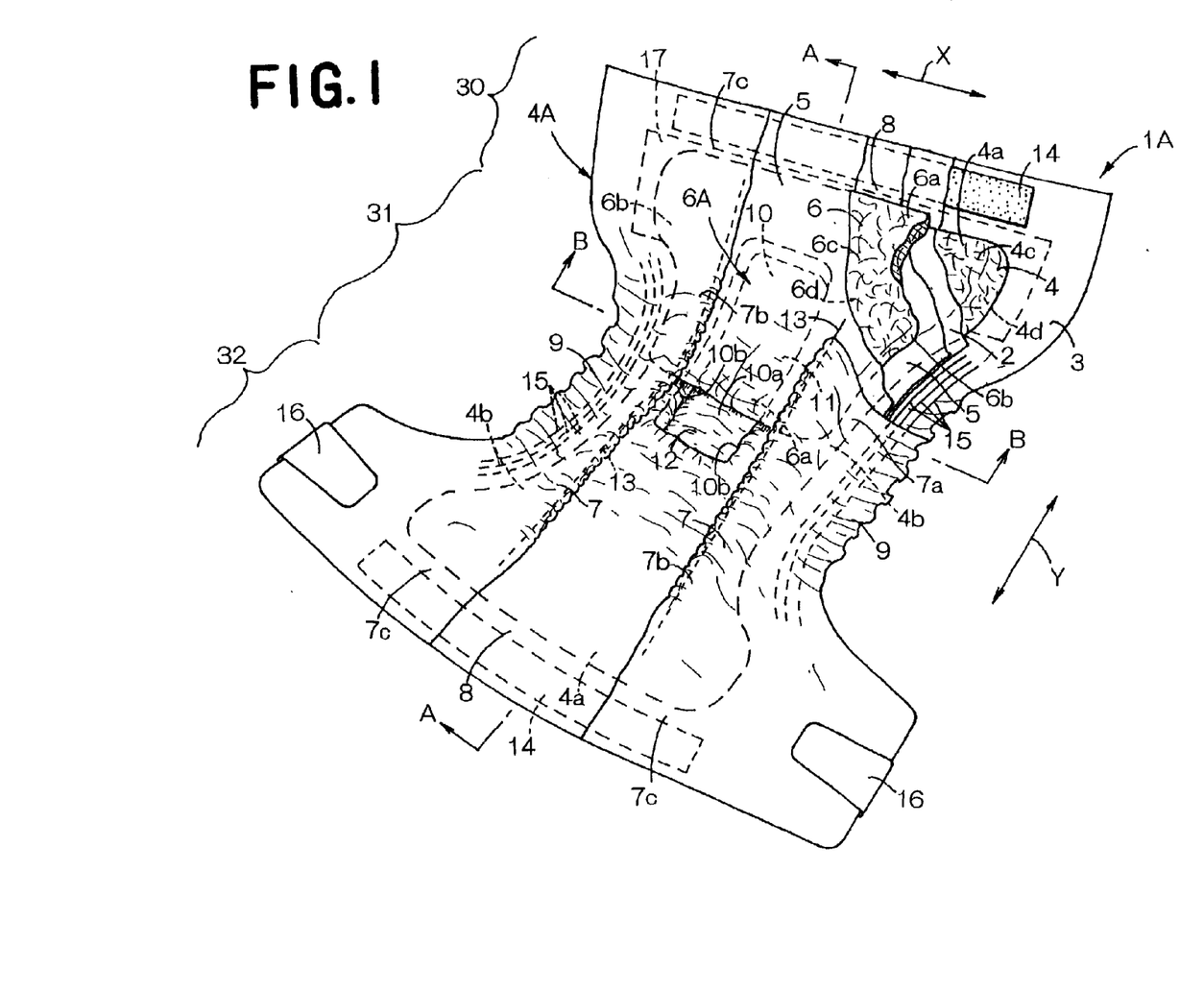
FIG. 1 is a partially cutaway perspective view showing the diaper as viewed from the side of the topsheet.
Figure 2:
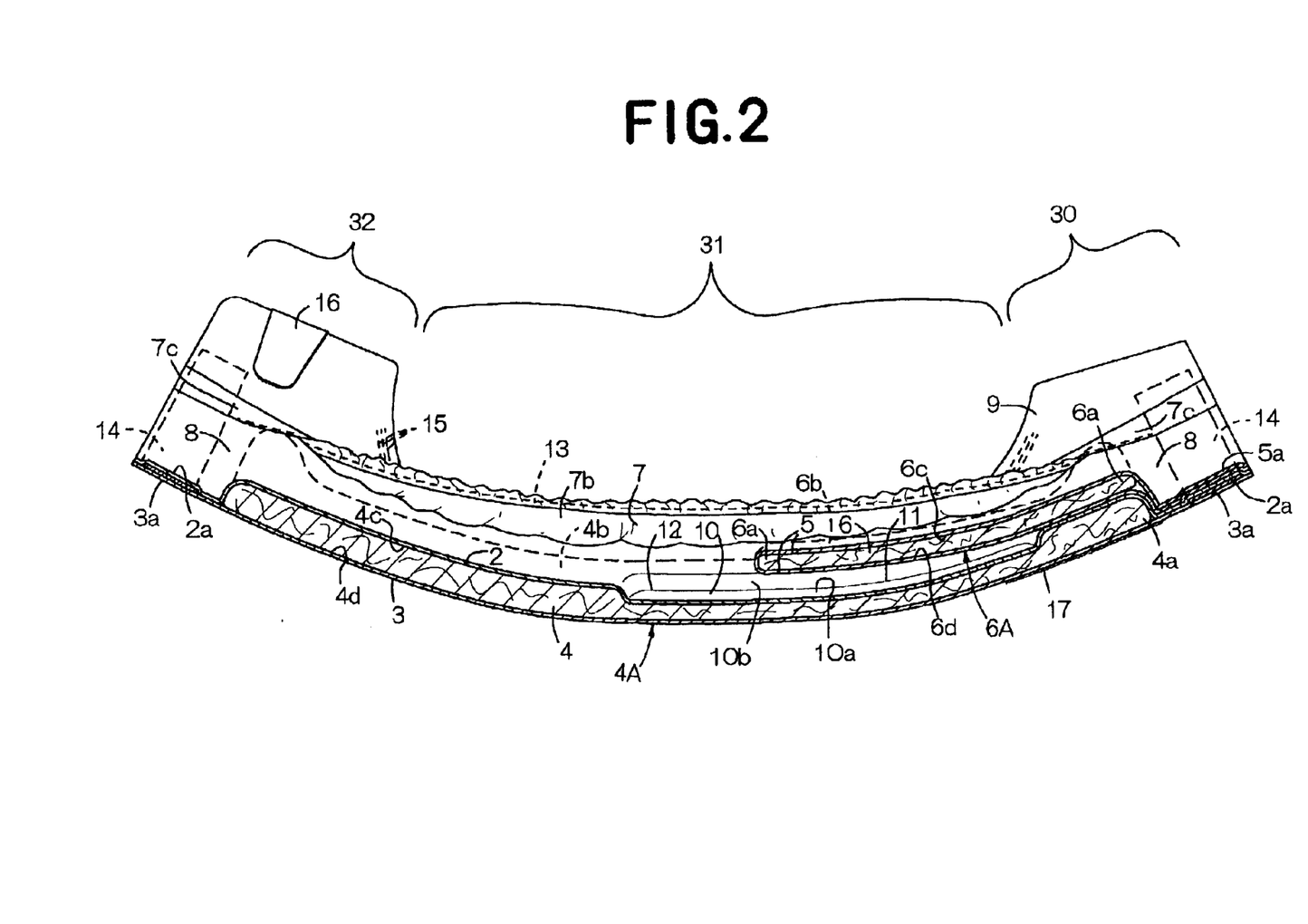
FIG. 2 is a cross-sectional view taken along a line A—A in FIG. 1.
Figure 3:
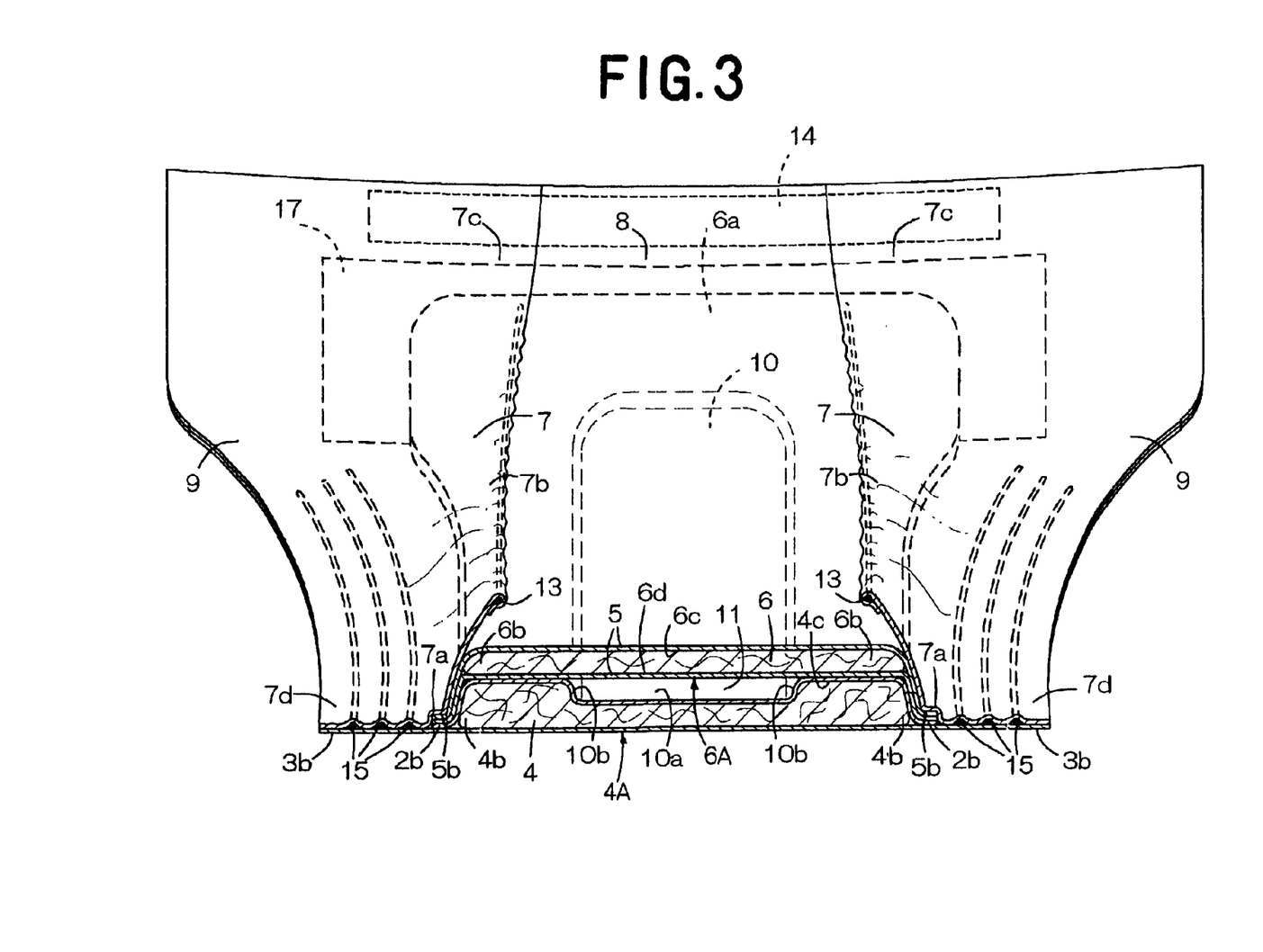
FIG. 3 is a cross-sectional view taken along a line B—B in FIG. 1.
Figure 4:
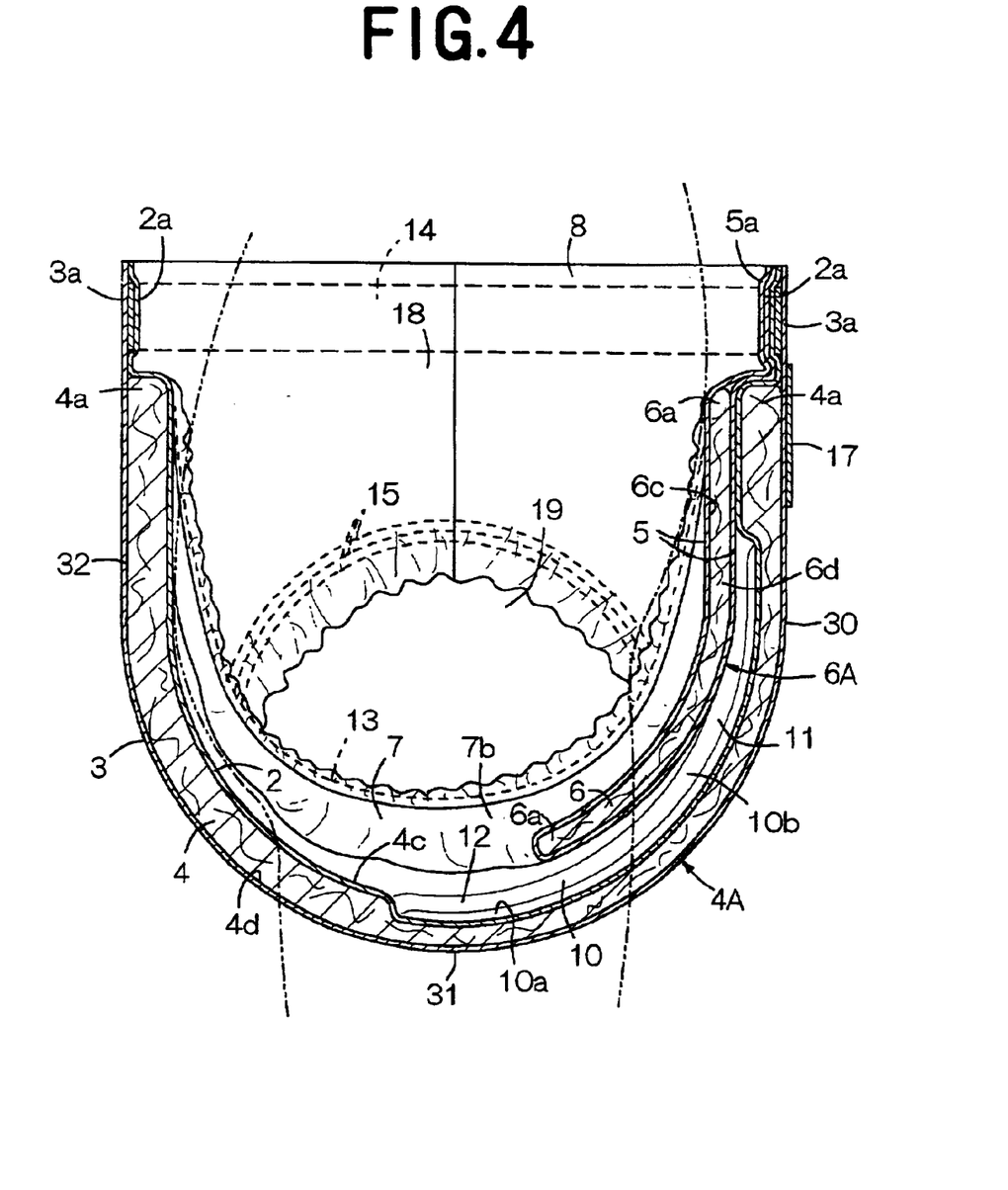
FIG. 4 is a partially cutaway cross-sectional view showing the diaper of FIG. 1 as put on the wearer's body with front and rear waist regions connected to each other.

FIG. 1 is a partially cutaway perspective view showing a diaper 1A as viewed from the side of a topsheet 2, FIG. 2 is a cross-sectional view taken along a line A—A in FIG. 1, FIG. 3 is a cross-sectional view taken along a line B—B in FIG. 1 and FIG. 4 is a partially cutaway cross-sectional view showing the diaper 1A of FIG. 1 as put on the wearer's body with front and rear waist regions 30, 32 connected to each other. In FIG. 1, a transverse direction is indicated by an arrow X and a longitudinal direction is indicated by an arrow Y.

The diaper 1A comprises a basic absorbent batt structure 4A composed of a liquid-pervious topsheet 2, a liquid-impervious backsheet 3, a liquid-absorbent core 4 disposed therebetween, a supplementary absorbent batt structure 6A composed of a liquid-absorbent core 6 covered with a liquid-pervious sheet 5, and substantially liquid-impervious barrier cuffs 7. The diaper 1A has a front waist region 30, a rear waist region 32 and a crotch region 31 extending between the front and rear waist regions 30, 32.

The core 4 extends across the crotch region 31 into the front and rear waist regions 30, 32. The contour of the core 4 is defined by longitudinally opposite ends 4a transversely extending in the front and rear waist regions 30, 32 and transversely opposite side edges 4b longitudinally extending between these two ends 4a. A pair of end flaps 8 transversely extend outside the respective ends 4a of the core 4. A pair of side flaps 9 longitudinally extend outside the side edges 4b of the core 4. In the crotch region 31, the side flaps 9 curve inwardly to the transverse direction of the diaper 1A in a shape of circular arcs, respectively. The core 4 has its upper surface 4c covered with the topsheet 2 to define a body facing surface of the batt structure 4A and its lower surface 4d covered with the backsheet 3 to define a garment facing surface of the batt structure 4A. These surfaces 4c, 4d are joined to the topsheet 2 and the backsheet 3, respectively.

The batt structure 4A is provided in its transversely middle region with a cavity 10 concaved from the body facing surface to its thickness direction. The cavity 10 extends in the longitudinal direction from the crotch region 31 toward the front waist region 30 and terminates in the vicinity of the ends 4a of the core 4. The cavity 10 has a bottom surface 10a and a pair of side surfaces 10b, to both of which the topsheet 2 is joined.

The batt structure 6A is placed upon the body facing surface of the batt structure 4A and extends from the front waist region 30 toward the crotch region 31. The contour of core 6 is defined by longitudinally opposite ends 6a transversely extending across the front waist region 30 and the crotch region 31, respectively, and transversely opposite side edges 6b longitudinally extending between these two ends 6a.

The core 6 has its upper surface 6c and its lower surface 6d covered with and joined to the liquid-pervious sheet 5 to define a body facing surface and an opposite inner surface, respectively. The liquid-pervious sheet 5 is folded along the ends 6a of the core 6 and then extends toward the end flaps 8.

In the diaper 1A, the batt structure 6A completely covers the upper opening of the cavity 10 in the front waist region 30 and partially covers this opening in the crotch region 31. The batt structure 4A, 6A are joined to each other in the vicinities of longitudinally opposite ends 4a, 6a and the transversely opposite side edges 4b, 6b of the cores, 4, 6 respectively with the topsheet 2 and the liquid-pervious sheet 5 lying therebetween.

The diaper 1A is provided with a feces receiving space 11 surrounded by the opposite inner surface of the batt structure 6A, and the bottom surface 10a and the side surface 10b of the cavity 10. The space 11 extends from the crotch region 31 toward the front waist region 30. In the crotch region 31 of the diaper 1A, the upper opening of the cavity 10 is not completely covered by the batt structure 6A but partially uncovered to provide an inlet 12 for feces to be led to the space 11.

Each of the cores 4, 6 comprises a mixture of fluff pulp and super-absorbent polymer particles or a mixture of fluff pulp, super-absorbent polymer particles and thermoplastic synthetic resin fiber compressed to a desired thickness. Preferably, the cores 4, 6 are entirely covered with tissue paper in order to prevent the polymer particles from falling off and/or to prevent deformation of the shapes of the cores 4, 6. The polymer particles may be selected from a group consisting of starch-, cellulose- and synthetic-polymer particles.

The barrier cuffs 7 lie on the side flaps 9 and extend in the longitudinal direction. The cuffs 7 respectively have proximal side edges 7a extending in the longitudinal direction immediately outside the transversely opposite side edges 4b of the core 4, distal side edges 7b extending in parallel to the proximal side edges 7a and normally biased to rise on the surface body facing surface of the batt structure 4A and longitudinally opposite fixed ends lying in the front and rear waist regions 30, 32 and collapsed inwardly in the transverse direction of the diaper 1A. In the cuffs 7, the proximal side edges 7a are joined to the side flaps 9 and the fixed ends 7c are joined to the end flaps 8, respectively.

The cuffs 7 further include lateral regions 7d extending transversely to the outward direction from the respective proximal side edges 7a. The distal side edges 7b are provided with elastic members 13 extending in the longitudinal direction and secured under tension to the respective distal side edges 7b. Each of the elastic members 13 is covered with a part of each of the its corresponding distal side edges 7b.

The diaper 1A curves itself in the longitudinal direction with the topsheet 2 inside and contraction of the elastic members 13 causes the distal side edges 7b of the cuffs 7 to uprise on the body facing surface of the batt structure 4A. In the front waist region 30, the distal side edges 7b of the cuffs 7 uprise on the body facing surface of the batt structure 6A.

The end flaps 8 are provided with ribbon-like elastic members 14 extending in the transverse direction and secured under tension to the respective end flaps 8 so as to be operatively associated with a waist-hole. In the crotch region 31, the side flaps 9 are respectively provided with a plurality of string-like elastic members 15 extending in the longitudinal direction and secured under tension to the respective side flaps 9 so as to be operatively associated with leg-holes.

In the rear waist region 32, proximal end regions of tape fasteners 16 are attached to the respective side flaps 9 so that these tape fasteners 16 may extend transversely inward. The tape fasteners 16 are coated on their distal end regions with a self-adhesive agent (not shown). In the front waist region 30, the backsheet 3 is provided on its outer surface with a rectangular target tape strip 17 formed of a plastic film and serving as a landing zone for the tape fasteners 16.

In the end flaps 8, longitudinally opposite end regions 2a of the topsheet 2 as well as longitudinally opposite end regions 3a of the backsheet 3 extend longitudinally outward beyond the longitudinally opposite ends 4a of the core 4 and are overlaid and joined to each other in these extended regions, as will be best seen in FIG. 2. Longitudinally opposite end regions 5a of the liquid-pervious sheet 5 extending longitudinally outward beyond one end of the core 6 are overlaid and joined to each other as well as to the associated one end region 2a of the topsheet 2. The elastic members 14 operatively associated with the waist-hole are interposed between the end regions 2a of the topsheet 2 and the end regions 3a of the backsheet 3 and secured to these end regions 2a, 3a.

In the side flaps 9, transversely opposite side edge regions 2b of the topsheet 2 extend transversely outward slightly beyond the side edges 4b of the core 4 and transversely opposite side edge regions 3b of the backsheet 3 as well as the lateral regions 7d of the cuffs 7 further extend transversely outward beyond the side edge regions 2b of the topsheet 2, as will be best seen in FIG. 3. The side edge regions 2b are interposed between the side edge regions 3b and the lateral regions 7d and joined to these regions 3b, 7d. The side edge regions 3b and the lateral regions 7d are overlaid and joined to each other.

Transversely opposite side edge regions 5b of the liquid-pervious sheet 5 extending transversely outward beyond side edges of the core 6 are overlaid and joined to each other, interposed between the side edge regions 2b of the topsheet 2 and the proximal side edges 7a of the cuffs 7, and joined to these regions 2b, 7a. The elastic members 15 operatively associated with the leg-holes are interposed between the edge regions 3b of the backsheet 3 and the side lateral regions 7d of the cuffs 7 and joined to these regions 3b, 7d.

To wear the diaper 1A, the side flaps 9 in the rear waist region 32 are placed upon the outer side of the side flaps 9 in the front waist region 30 and the free end regions of the respective tape fasteners 16 are anchored on the target tape strip 17 by means of adhesive to connect the front and rear waist regions 30, 32 to each other. With the diaper 1A having the front and rear waist regions 30, 32 connected to each other in this manner, a waist-hole 18 and a pair of leg-holes 19 are defined.

Even when a wearer's body weight is exerted upon the diaper 1A from the side of the body facing surface of the batt structure 6A downward to the thickness direction of the diaper 1A and the space 11 is, in consequence, slightly compressed, it is not likely that this space 11 might be completely compressed.

Even when a large quantity of loose passage or watery feces is discharged on the diaper 1A in the crotch region 31 and spreads on the topsheet toward the front waist region 30, most of such loose passage or watery feces is guided through the inlet 12 for feces into the space 11. This diaper 1A is free from an anxiety that such feces might move onto the batt structure 6A core 6 and therefore can reliably prevent, in the front waist region 30, any quantity of feces from clinging to a wearer's skin. After such loose passage or watery feces has been received in the space 11, a water portion of the feces is absorbed and contained by the batt structure 4A, 6A while a solid-portion thereof is retained in the space 11.

The cuffs 7 with the uprising distal side edges 7b provide barriers against body wastes and prevent the body wastes from leaking beyond the side flaps 9.

Figure 5:
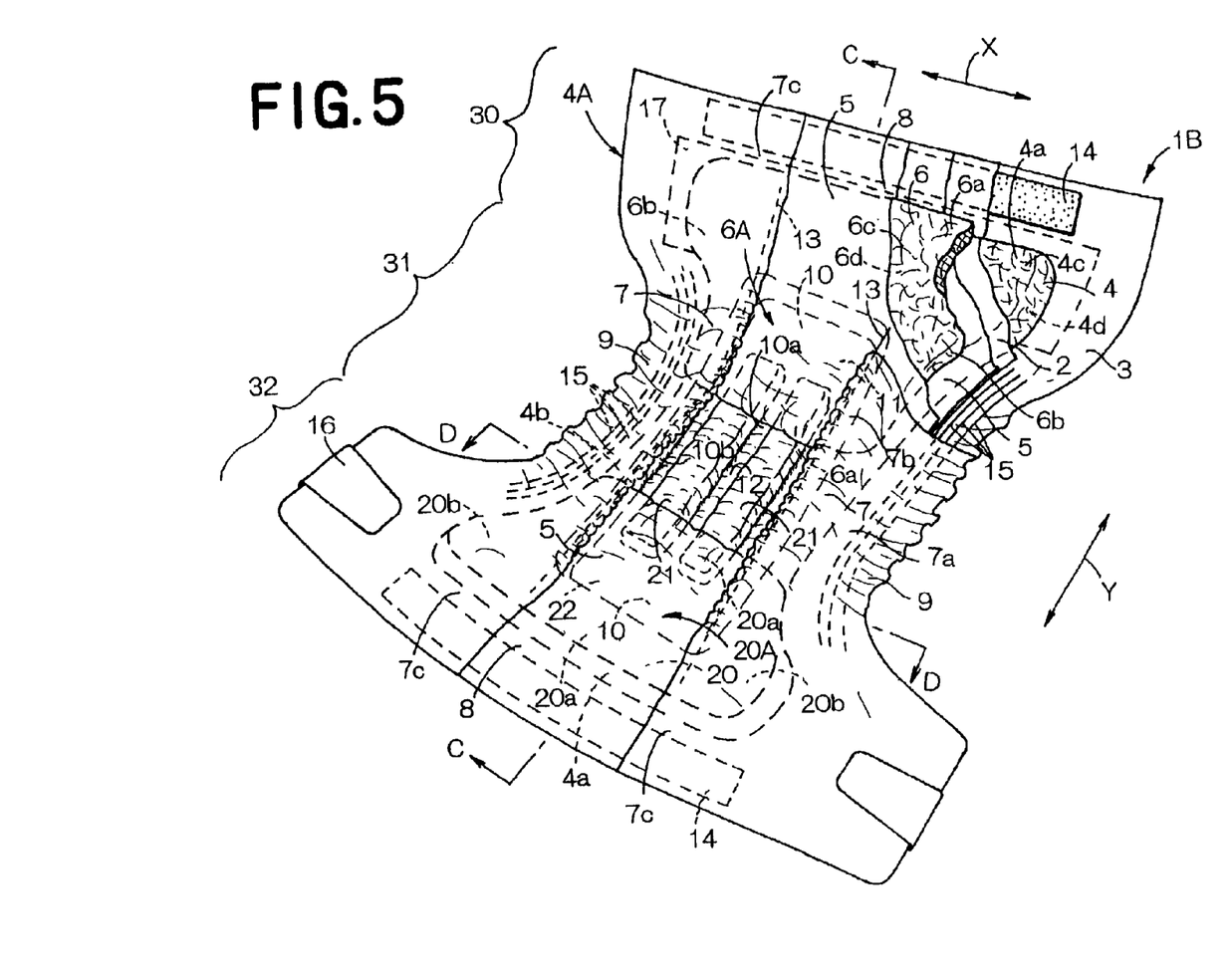
FIG. 5 is a partially cutaway perspective view showing another embodiment of the diaper.
Figure 6:
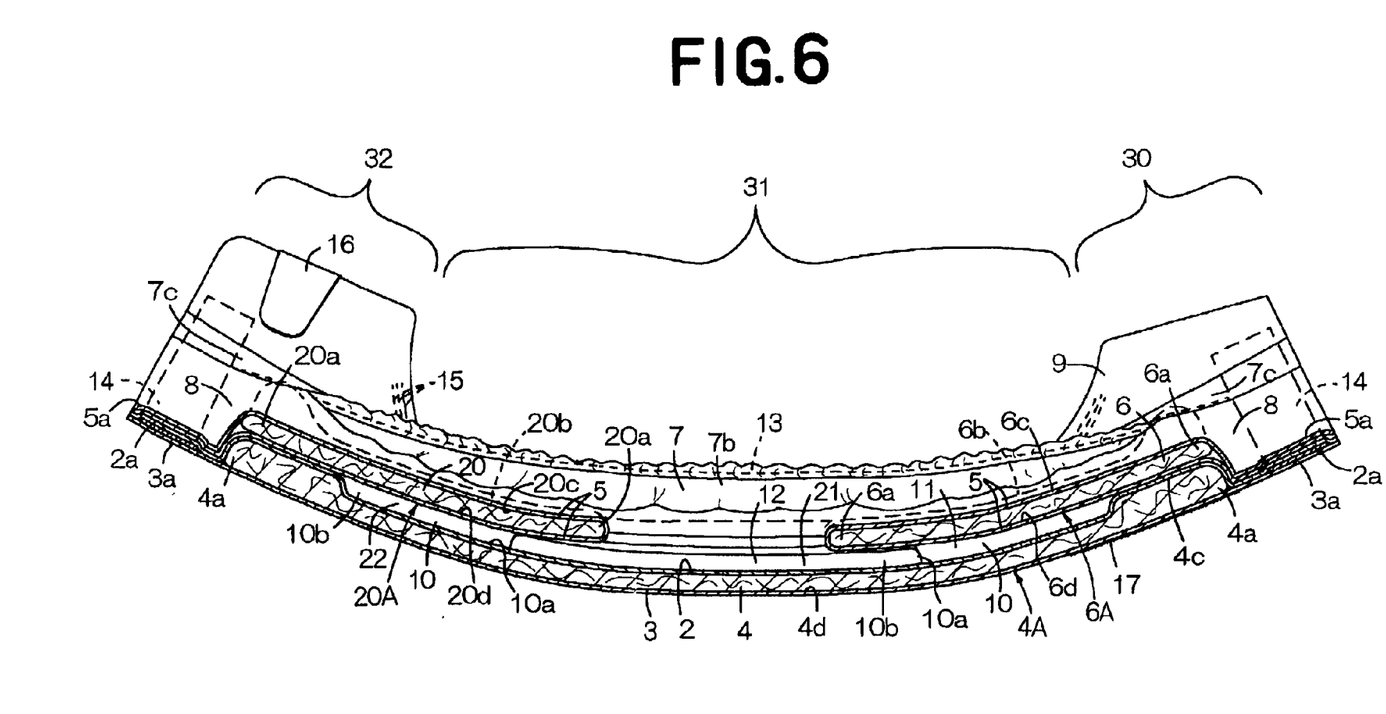
FIG. 6 is a cross-sectional view taken along a line C—C in FIG. 5.
Figure 7:
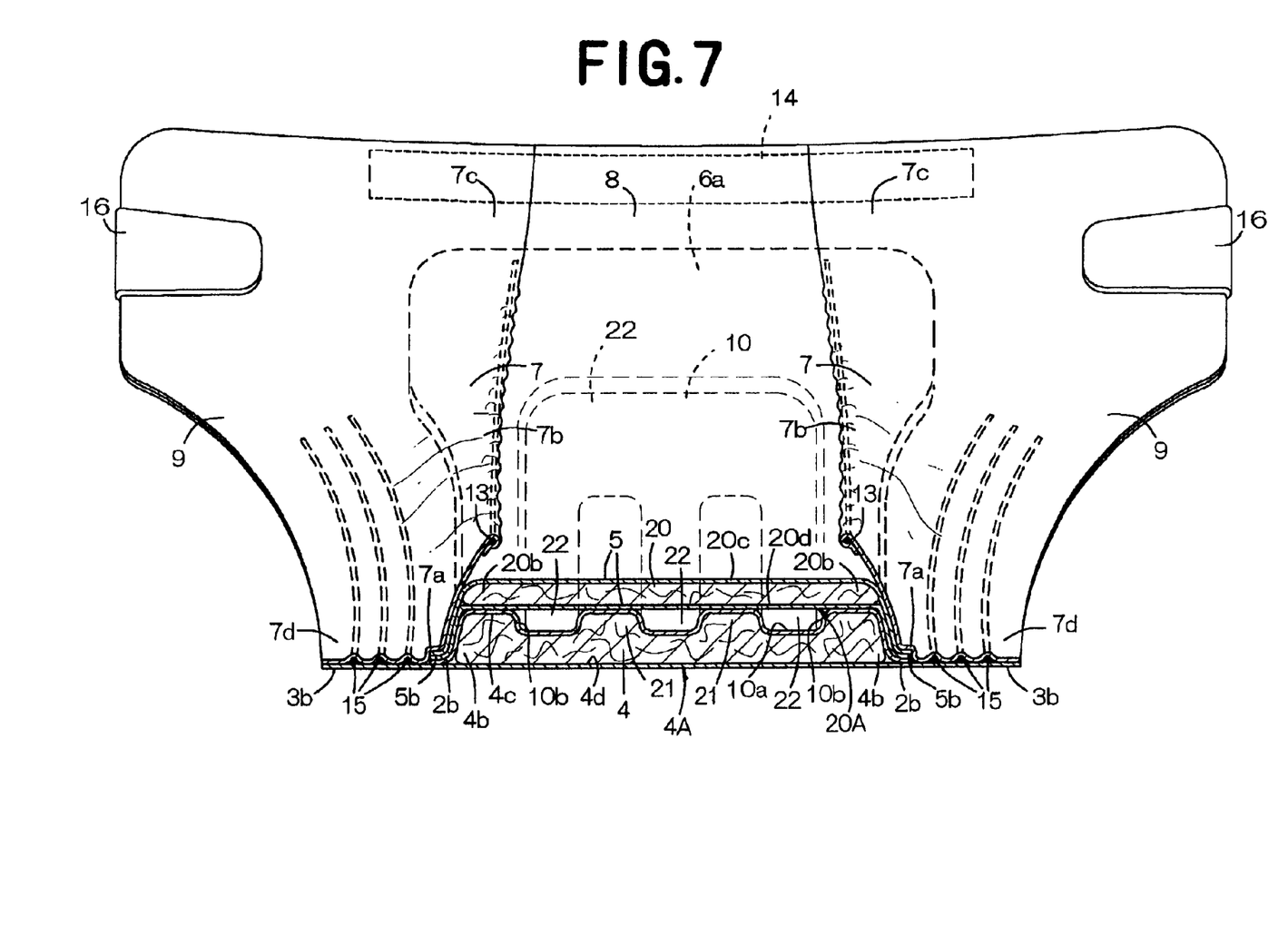
FIG. 7 is a cross-sectional view taken along a line D—D in FIG. 5.
Figure 8:
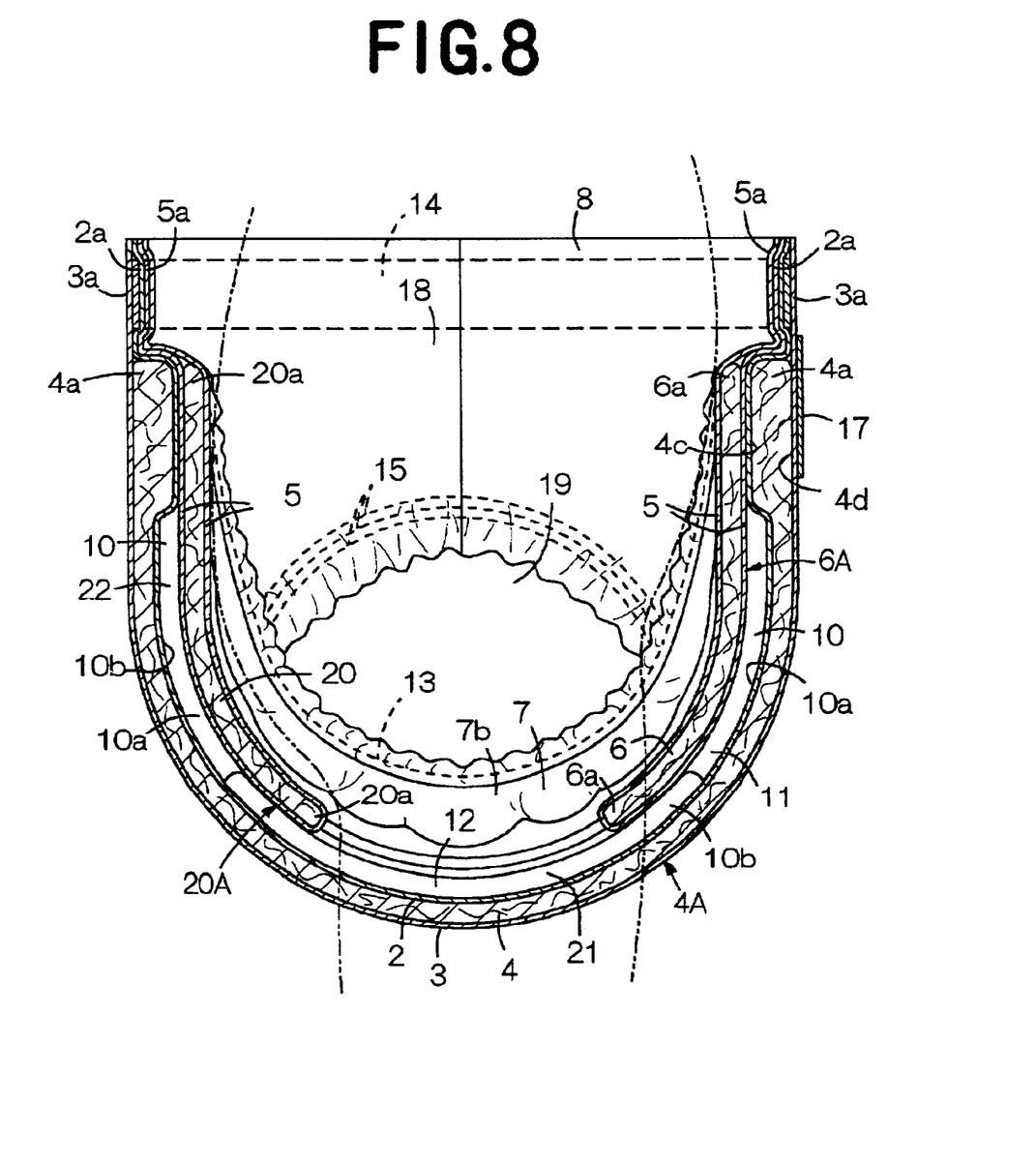
FIG. 8 is a partially cutaway cross-sectional view showing the diaper of FIG. 5 as put on the wearer's body with the front and rear waist regions connected to each other.

FIG. 5 is a partially cutaway perspective view showing another embodiment 1B of the diaper, FIG. 6 is a cross-sectional view taken along a line C—C in FIG. 5, FIG. 7 is a cross-sectional view taken along a line D—D in FIG. 5 and FIG. 8 is a partially cutaway cross-sectional view showing the diaper 1B of FIG. 5 as put on the wearer's body with the front and rear waist regions 30, 32 connected to each other.

In the case of this diaper 1B, the batt structure 4A is formed in its transversely middle region with the cavity 10 extending from the crotch region 31 toward the front waist region 30 and the rear waist region 32. The cavity 10 terminates in the vicinity of the longitudinally opposite ends 4a of the batt structure 4A. The diaper 1B includes a second supplementary batt structure 20A having a liquid-absorbent core 20 placed upon the body facing surface of the batt structure with the topsheet 2 lying therebetween.

In the crotch region 31, the batt structure 4A is formed with a plurality of walls 21 protruding upward from the bottom surface 10a of the cavity 10 and extending in the longitudinal direction. These walls 21 are transversely spaced one from another by a given interval. Thus, the cavity 10 is divided in the transverse direction. The topsheet 2 is placed in close contact with the bottom surface 10a and the side surface 10b as well as with the respective walls 21 of the cavity 10.

The diaper 1B may be so arranged that these walls 21 extend from the crotch region 31 toward the front and rear waist regions 30, 32 and terminate in the vicinity of the longitudinally opposite ends of the core 4 wherein the cavity 10 is transversely divided, also in the front and rear waist regions 30, 32, by the walls 21.

The core 20 extends from the rear waist region 32 toward the crotch region 31. The contour of core 20 is defined by longitudinally opposite ends 20a transversely extending across the rear waist region 32 and the crotch region 31, respectively, and transversely opposite side edges 20b longitudinally extending between the ends 20a.

The core 20 has its upper surface 20c and its lower surface 20d both covered with the liquid-pervious sheet 5 to define a body facing surface and an opposite inner surface of a second supplementary absorbent batt structure 20A, respectively and these surfaces 20c, 20d are joined to the liquid-pervious sheet 5. The liquid-pervious sheet 5 is folded back along the end 20a of the core 20 lying on the side of the crotch region 31 and then extends toward the rear end flap 8.

In the diaper 1B, the batt structure 20A completely covers the upper opening of the cavity 10 in the rear waist region 32 and partially covers this opening in the crotch region 31. The batt structure 4A, 20A are joined to each other in the vicinities of longitudinally opposite ends 4a, 20a and the transversely opposite side edges 4b, 20b of the cores 4, 20, respectively with the topsheet 2 and the liquid-pervious sheet 5 lying therebetween.

The core 20 comprises a mixture similar to those forming the cores 4, 6 and is compressed to a desired compressed, preferably, the core 20 is also entirely covered with tissue paper.

The diaper 1B is provided with a feces receiving space 22 surrounded by the inner surface of the batt structure 20A, and the bottom surface 10a and the side surface 10b of the cavity 10. The space 22 extends from the crotch region 31 toward the rear waist region 32. In the crotch region 31 of the diaper 1B, the upper opening of the cavity 10 is exposed between the vicinities of the end 6a of the core 6 and the end 20a of the core 20 to form an inlet 12 for feces being contiguous to the spaces 11, 12.

The liquid-pervious sheet 5 folded back along the inner end 20a so as to extend longitudinally outward has opposite end regions 5a placed upon and joined to each other and then joined also to the associated end region 2a of the topsheet 2 as will be best seen in FIG. 6. The longitudinally opposite fixed end regions 7c of the respective cuffs 7 are joined to the end regions 5a of the liquid-pervious sheet 5.

As will be seen in FIG. 7, the transversely opposite side edge regions 5b of the liquid-pervious sheet 5 extending transversely outward beyond transversely opposite side edges 20b of the core 20 are placed upon and joined to each other. These side edges 20b joined together are interposed between the transversely opposite side edge regions 2b of the topsheet 2 and the proximal side edges 7a of the cuffs 7 and joined to these regions 2b, 7a.

Feces discharged onto the diaper 1B can be received not only by the space 11 but also by the space 22, preventing any quantity of feces from leaking beyond the end flaps 8 in the rear waist region 32. With this diaper 1B, it makes it possible to prevent any quantity of feces from clinging to a wearer's skin in the front waist region 30 as well as in the rear waist region 32.

A plurality of walls 21 transversely extending across the core 4 in the crotch region 31 serve as barriers to prevent feces from flowing sideways. The inner ends 6a, 20a of the core 6 and the core 20 are placed upon the walls 21 in the crotch region 31 and the walls 21 support a wearer's body weight exerted on the diaper 1B downward in its thickness direction. In this way, the spaces 11, 22 are more resistant to compression by its wearer's weight than in the diaper 1A shown by FIG. 1.

Figure 9:
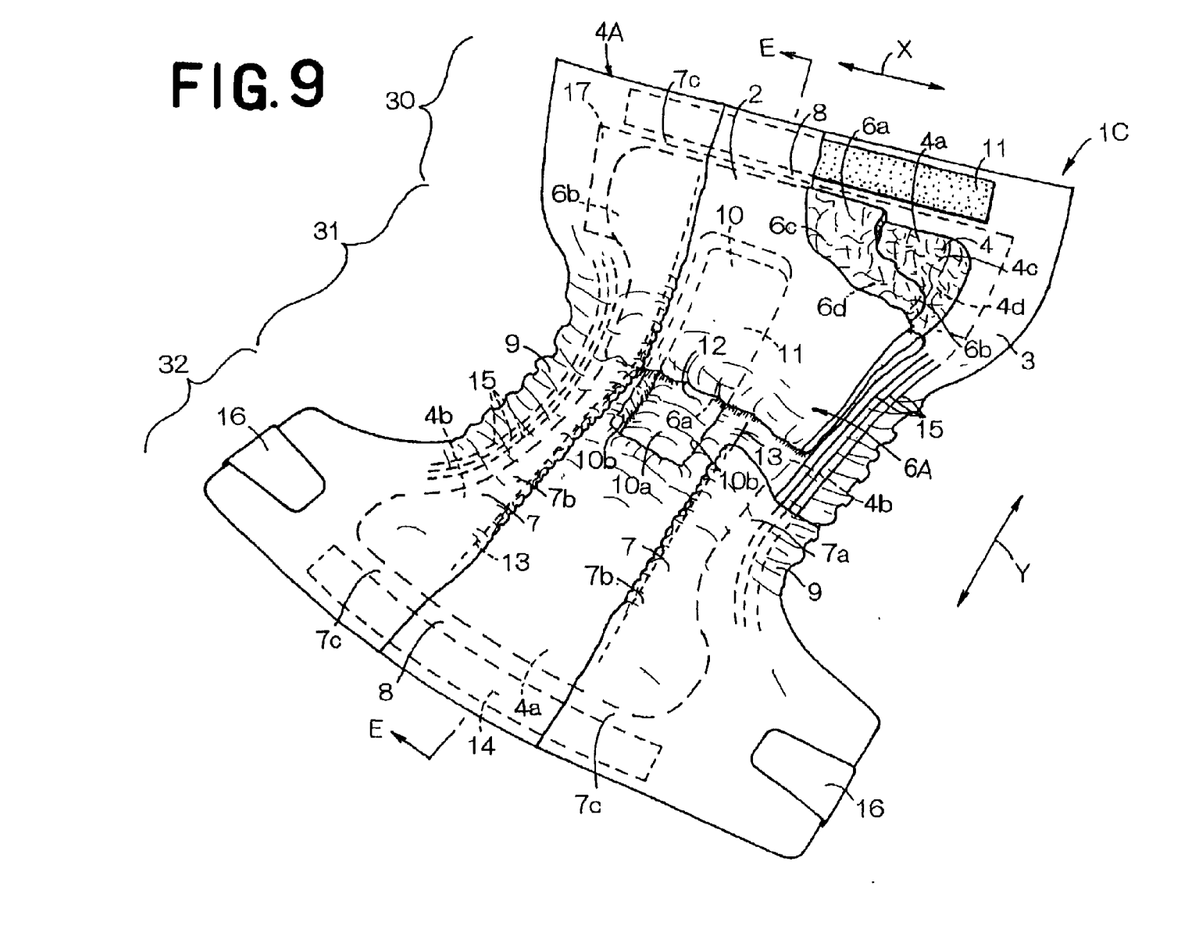
FIG. 9 is a partially cutaway perspective view showing still another embodiment of the diaper.
Figure 10:
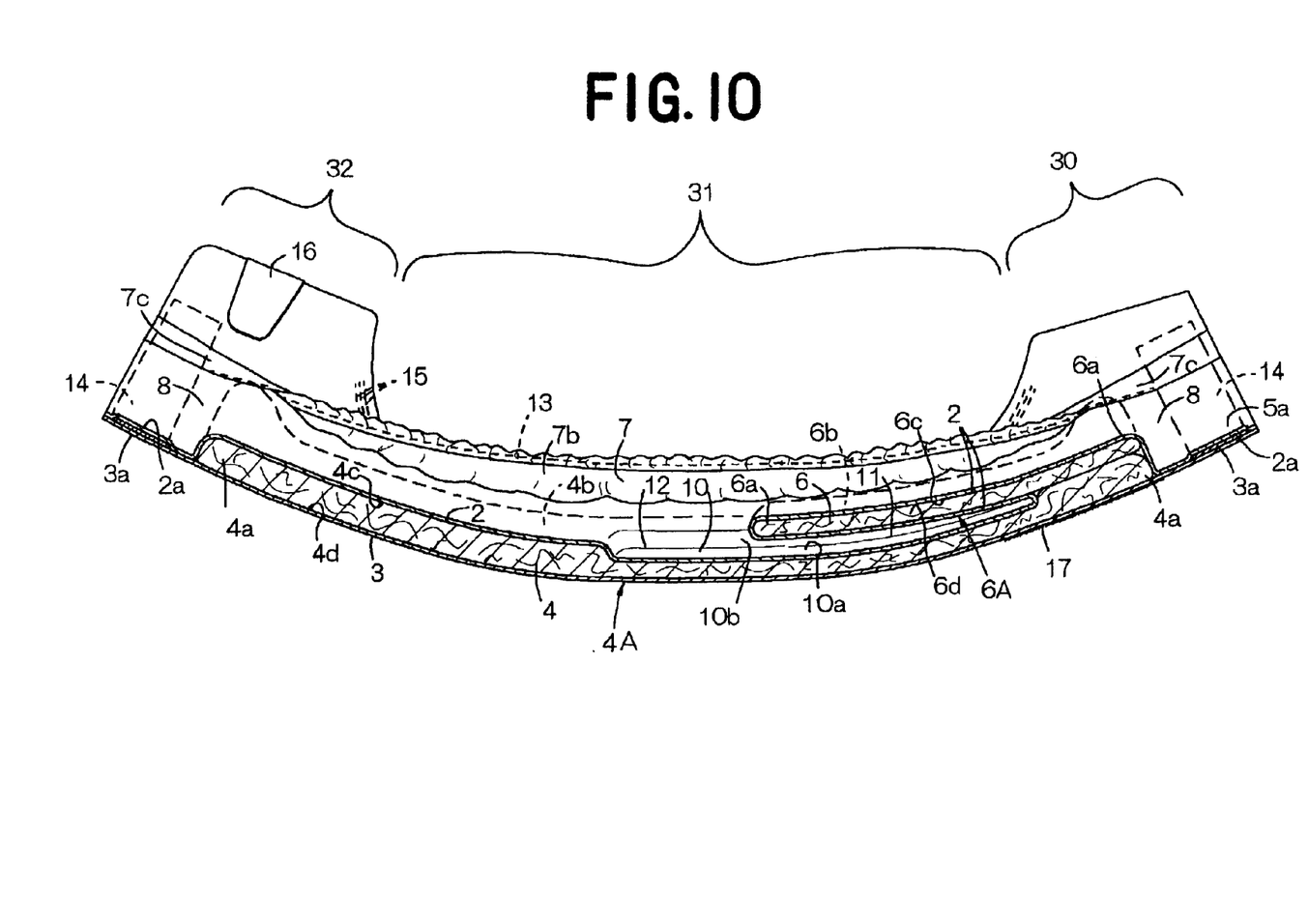
FIG. 10 is a cross-sectional view taken along a line E—E in FIG. 9.

FIG. 9 is a partially cutaway perspective view showing still another embodiment 1C of the diaper and FIG. 10 is a cross-sectional view taken along a line E—E in FIG. 9.

In this diaper 1C, the batt structures 4A, 6A placed upon the body facing surface 4c of the batt structure 4A are interposed between the topsheet 2 and the backsheet 3. The topsheet 2 is folded back in the inner end 6a of the core 6 onto the surface 6c of the core 6 and tucked between the surface 4c of the core 4 and the surface 6d of the core 6.

In this diaper 1C, the surface 6c of the core 6 is covered with the topsheet 2 while the surface 6d of the core 6 facing away except its outer end 6a and the surface 4c of the core 4 are also covered with the topsheet 2. The topsheet 2 is joined to these surfaces 4c, 6c, 6d. The topsheet 2 interposed between the cores 4, 5 is placed in close contact with the surface 6c of the core 6 as well as with the bottom surface 10a and the side surface 10b of the cavity 10.

Similar to the diaper 1A shown in FIG. 1, this diaper 1C is formed with the feces receiving space 11 surrounded by the body facing surface of the batt structure 6A and the bottom and side surfaces 10a, 10b of the cavity 10. The space 11 extends from the crotch region 31 toward the front waist region 30. In the crotch region 31 of the diaper 1C, the upper opening of the cavity 10 is not completely covered by the second core 6 and is partially uncovered to provide the inlet 12 for the space 11.

The topsheet 2 and the liquid-pervious sheet 5 may be formed of a hydrophilic fibrous nonwoven fabric or a finely porous plastic film. The backsheet 3 may be formed of a hydrophobic a fibrous nonwoven fabric, a liquid-impervious plastic film, two-layers of hydrophobic fibrous nonwoven fabric laminated with each other or a composite sheet consisting of a hydrophobic fibrous nonwoven fabric and a plastic film bonded to this hydrophobic fibrous nonwoven fabric. The barrier cuffs 7 may be formed of a hydrophobic fibrous nonwoven fabric.

It is also possible to form the backsheet 3 and the barrier cuffs 7 using a composite nonwoven fabric consisting of melt blown fibrous nonwoven fabric having a good water-resistant property sandwiched between two layers of spun bond fibrous nonwoven fabric having high strength and flexibility.

Nonwoven fabric used herein may be selected from a group including those obtained by spun lace-, needle punch-, melt blown-, thermal bond-, spun bond-, chemical bond- and air through-processes. Component fiber of such nonwoven fabric may be selected from a group consisting of polyolefine-, polyester- and polyamide-based fibers and core-sheath type or side-by-side type conjugated fiber of polyethylene/polypropylene or polyethylene/polyester.

Joining of the top- and backsheets 2, 3, the liquid-pervious sheet 5 and the barrier cuffs 7 as well as attachment of the cores 4, 6, 20, and the elastic members 13, 14, 15 to these top- and backsheets 2, 3 and liquid-pervious sheet 5 may be carried out using hot melt adhesive or welding technique such as heat-sealing or ultrasonic sealing.

This invention is applicable not only to a diaper of open-type but also to a diaper of pants-type having its front and rear waist regions connected in advance to each other.

The disposable diaper according to this invention is primarily characterized in that the feces receiving space is formed between the supplementary absorbent batt structure and the cavity so as to extend from the crotch region toward the front waist region and feces discharged onto the diaper is guided through the inlet for feces into the space. Specifically, it is not likely that such feces might move onto the supplementary absorbent batt structure and therefore the diaper according to this invention can reliably prevent, in the front waist region, any quantity of feces from clinging to its wearer's skin. While a wearer's body weight exerted on the diaper from the body facing surface of the supplementary absorbent batt structure in the direction of the diaper's thickness may slightly compress the space, there is no anxiety that the space might be completely compressed.

With the diaper according to another embodiment of this invention in which the cavity extends from the crotch region toward the front and rear waist regions and there is provided the second supplementary absorbent batt structure, feces discharged onto the diaper is received not only by the space defined between the supplementary absorbent batt structure and the cavity but also by the space defined between the second supplementary absorbent batt structure and the cavity. Such a unique arrangement is particularly advantageous in that a risk of leaking of feces in the rear waist region occurring beyond the end flaps as well as a risk of clinging of feces to a wearer's skin occurring in the front and rear waist regions can be reliably avoided.

With the diaper according to the embodiment of this invention in which the cavity of the first core is provided with a plurality of walls, these walls serve as barriers against feces to flow sideways.

What is claimed is:

1. A disposable diaper having a front waist region, a rear waist region and a crotch region therebetween, said diaper comprising:

a basic absorbent batt structure having a liquid-pervious body facing surface and a liquid-impervious garment facing surface;

at least one supplementary absorbent batt structure having a liquid-pervious body facing surface and an opposite inner surface;

said supplementary absorbent batt structure being placed upon the body facing surface of said basic absorbent batt structure so as to extend from said front waist region toward said crotch region;

said basic absorbent batt structure being formed in a transversely middle region of the body facing surface thereof with a cavity which extends from said crotch region toward said front waist region;

said supplementary absorbent batt structure covering an upper opening of said cavity in said front waist region and partially covering said upper opening of said cavity in said crotch region; and a front excrement receiving space being formed between said supplementary absorbent batt structure and said cavity so as to extend from said crotch region toward said front waist region, and said upper opening of said cavity being partially uncovered in said crotch region to define an inlet leading into said front excrement receiving space.

2. A disposable diaper according to claim 1, wherein said basic absorbent batt structure comprises a liquid-pervious topsheet defining said body facing surface thereof, a liquid-impervious backsheet defining said garment facing surface thereof and a liquid-absorbent first core disposed therebetween.

3. A disposable diaper according to claim 2, wherein said basic absorbent batt structure further comprises a pair of elasticized side flaps extending outwardly from transversely opposite side edges of said first core.

4. A disposable diaper according to claim 3, wherein said side flaps are elasticized by elastic members secured therealong.

5. A disposable diaper according to claim 3, further comprising barrier cuffs having proximal edge portions joined onto said side flaps.

6. A disposable diaper according to claim 1, wherein said supplementary absorbent batt structure comprises a liquid-absorbent second core and a liquid-pervious sheet covering at least a body facing surface of said second core.

7. A disposable diaper according to claim 1, further comprising at least a barrier cuff that extends outwardly from said supplementary absorbent batt structure.

8. A disposable diaper according to claim 1, further comprising barrier cuffs elasticized by elastic members secured along distal edge portions thereof.

9. A disposable diaper according to claim 8, wherein said distal edge portions of said barrier cuffs are positioned inwardly of proximal edge portions of said barrier cuffs.

10. A disposable diaper according to claim 1, further comprising:

another supplementary absorbent batt structure having a body facing surface and an opposite inner surface which is at least partially covered with a liquid-pervious sheet and extends from said rear waist region toward said crotch region on the body facing surface of said basic absorbent batt structure;

said cavity extending from said crotch region toward said front and rear waist regions;

the upper opening of said cavity being covered with said second supplementary absorbent batt structure in said rear waist region and partially covered with said second supplementary absorbent batt structure in said crotch region; and a rear excrement receiving space being formed between said second supplementary absorbent batt structure and said cavity so as to extend from said crotch region toward said rear waist region, wherein said inlet leading into both said front and rear excrement receiving spaces is formed between said two supplementary absorbent batt structures.

11. A disposable diaper according to claim 1, further comprising a plurality of walls protruding upward from the bottom of said cavity at a height substantially corresponding to a depth of said cavity;

wherein said walls extend in the longitudinal direction on the body facing surface of said basic absorbent batt structure and are transversely spaced one from another by a given interval so that said cavity is transversely divided by said walls.

12. A disposable diaper according to claim 11, wherein said walls extend in said crotch region but not in said front and rear waist regions.

\* \* \* \* \*